US008795228B2

(12) United States Patent
Rizq et al.

(10) Patent No.: US 8,795,228 B2
(45) Date of Patent: Aug. 5, 2014

(54) DRUG DELIVERY DEVICE WITH SHEATH FOR IMPROVED DRUG DELIVERY

(75) Inventors: Raed Rizq, Maple Grove, MN (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 71 days.

(21) Appl. No.: 13/462,231

(22) Filed: May 2, 2012

(65) Prior Publication Data
US 2012/0283636 A1 Nov. 8, 2012

Related U.S. Application Data (60) Provisional application No. 61/482,871, filed on May 5, 2011.

(51) Int. Cl.
*A61M 31/00* (2006.01)
*A61M 37/00* (2006.01)

(52) U.S. Cl.
USPC ................. 604/103.02; 604/103.06

(58) Field of Classification Search
CPC . A61M 25/10; A61M 25/1002; A61M 29/00; A61M 2025/105; A61M 2025/1075; A61M 2025/1031
USPC ................. 604/96.01–104, 915–921
See application file for complete search history.

(56) References Cited

U.S. PATENT DOCUMENTS

| 5,423,851 A | 6/1995 | Samuels |
| 5,693,014 A | 12/1997 | Abele et al. |
| 5,797,948 A | 8/1998 | Dunham |
| 5,810,767 A | 9/1998 | Klein |
| 6,048,332 A * | 4/2000 | Duffy et al. ............. 604/103.08 |
| 6,533,755 B2 | 3/2003 | Adams |
| 6,659,996 B1 * | 12/2003 | Kaldany ........................ 604/508 |
| 6,939,320 B2 | 9/2005 | Lennox |
| 7,070,613 B2 | 7/2006 | Weber et al. |
| 8,109,904 B1 * | 2/2012 | Papp ........................ 604/103.01 |

(Continued)

FOREIGN PATENT DOCUMENTS

| EP | 1825824 A1 | 8/2007 |
| WO | 2007/096856 A2 | 8/2007 |

(Continued)

OTHER PUBLICATIONS

European Patent Office, International Search Report and Written Opinion in International Application No. PCT/US2012/036089, dated Jul. 25, 2012.
European Patent Office, partial International Search Report in International Application No. PCT/US2012/041060, dated Sep. 21, 2012.

*Primary Examiner* — Quynh-Nhu H Vu
*Assistant Examiner* — Jenna Zhang
(74) *Attorney, Agent, or Firm* — Fish & Richardson P.C.

(57) ABSTRACT

A drug eluting balloon device is disclosed, comprising a balloon and a sheath disposed around the balloon, the sheath comprising a plurality of drug delivery areas. When the sheath is in a first position, the drug delivery areas are in the form of pockets adapted to contain a therapeutic agent. When the sheath is expanded, the pockets invert into protrusions in order to deliver the therapeutic agent. In an alternative embodiment, the pockets are adapted to be pushed outwardly upon inflation of the balloon. The device may further comprise a fluid or shape memory material to force the pockets outwardly.

13 Claims, 4 Drawing Sheets

(56) References Cited

U.S. PATENT DOCUMENTS

| | | |
|---|---|---|
| 2011/0054396 A1 | 3/2011 | Kangas et al. |
| 2011/0054443 A1 | 3/2011 | Weber |
| 2011/0087191 A1 | 4/2011 | Scheuermann |
| 2011/0130829 A1 | 6/2011 | Clarke et al. |
| 2011/0152765 A1 | 6/2011 | Weber et al. |
| 2011/0301565 A1 | 12/2011 | Weber |
| 2012/0053517 A1* | 3/2012 | Chen et al. ............... 604/103.02 |
| 2012/0283636 A1 | 11/2012 | Rizq et al. |

FOREIGN PATENT DOCUMENTS

| | | |
|---|---|---|
| WO | 2009/036118 A1 | 3/2009 |
| WO | 2010/024871 A1 | 3/2010 |
| WO | WO 2010024871 A1 * | 3/2010 |
| WO | 2010/080575 A2 | 7/2010 |
| WO | WO 2010080575 A2 * | 7/2010 |
| WO | 2011/094476 A1 | 8/2011 |

\* cited by examiner

DRUG DELIVERY DEVICE WITH SHEATH FOR IMPROVED DRUG DELIVERY

CROSS REFERENCE TO RELATED APPLICATION

The present application claims priority to U.S. provisional application Ser. No. 61/482,871 filed May 5, 2011, the disclosure of which is incorporated herein by reference in its entirety.

TECHNICAL FIELD

The present invention relates to medical devices, such as drug eluting balloon devices, for the delivery of medicaments to body tissue.

BACKGROUND

Numerous contemporary medical procedures deliver drugs directly to target sites of diseased tissue. This targeted delivery has proven to be an advantageous approach for treating various medical conditions. Using targeted delivery, a controlled dose of the drug may be delivered directly to a target site while avoiding or minimizing exposing other parts of the body to the drug. Also, greater amounts of drug may be delivered to the afflicted parts of the body. In one approach to localized drug delivery, a balloon catheter is used, wherein the balloon has drug on its outer surface and is expanded within a vessel to deliver the drug to the vessel wall.

One problem often encountered with these techniques is inadequate drug release (or inadequate control thereof) when the balloon is deployed. For example, in conventional drug eluting balloons, much of the drug can be lost due to washing away by the flow of blood as the balloon is being delivered to the target site.

In an effort to avoid these problems, certain drug eluting balloon systems include a sheath disposed around a balloon. In one example, a sheath is provided around a balloon with one or more holes in the sheath for containing the drug. As the balloon is expanded, the sheath expands as well, causing the drug within the holes to be released to the target site.

Such systems have drawbacks, however. For example, much of the drug can remain in the holes even after expansion. As a result, very little drug is released. In some cases, as little as 10%-20% of the drug is released to the target site. To compensate for this, such drug eluting balloons have been provided with large amounts of excess medicament in order to ensure that a target site receives an adequate dose. In addition to this wastefulness, these devices also have poor control over the dosage of drug delivered to the target site.

An additional drawback of these systems is the potentially substantial loss of medicament as the balloon moves through the vasculature to the target site. The time it takes to guide the balloon through the system, which varies widely between patients, further compounds this problem. This variation adds to the difficulty in predicting the amount of medicament lost as the device travels to a target site. As a result, ensuring that the proper amount of medicament actually reaches the target site becomes problematic.

Accordingly, there is a need for a drug eluting system that more effectively releases a medicament to a target site.

SUMMARY

The present invention generally relates to medical devices, such as drug eluting balloon devices.

In one embodiment, a drug eluting balloon device comprises an inflatable balloon, inflatable from a substantially deflated position to a substantially inflated position, and a longitudinal sheath disposed around the balloon, the longitudinal sheath being expandable from a first position to a second position. When the balloon is in the substantially deflated position the sheath is in the first position, and when the balloon is inflated to the substantially inflated position the sheath is expanded to the second position. The sheath comprises a plurality of drug delivery areas. When the sheath is in the first position, the drug delivery areas are in the form of pockets adapted to contain a therapeutic agent. The drug delivery areas are adapted to invert from pockets into protrusions upon inflation of the balloon and expansion of the sheath, such that the drug delivery areas deliver the therapeutic agent to a target site. The sheath may be comprised of a compliant material.

In further embodiments, in a stable condition of the sheath, the drug delivery areas of the sheath protrude outwardly as protrusions. The protrusions may be pressed inwardly to form the pockets. In such an embodiment, the pockets may be in a quasi-stable condition. Expansion of the sheath from the first position to the second position causes the drug delivery areas to self-invert from the pockets into the protrusions.

To facilitate drug delivery, areas of the sheath surrounding the pockets of the sheath may be stiffer than the pockets of the sheath, for example by being made of a stiffer material. The sheath may comprise a hydrophobic material.

In further embodiments, a reservoir may be provided to refill the pockets with therapeutic agent.

In another embodiment, a drug eluting balloon device comprises an inflatable balloon and a longitudinal sheath, the sheath comprising a plurality of pockets adapted to contain a therapeutic agent. Areas of the sheath surrounding the pockets of the sheath may be stiffer than the pockets of the sheath. This may be accomplished, for example, by making the areas of the sheath surrounding the pockets thicker than the areas of the sheath forming the bottoms of the pockets, or by making the areas of the sheath surrounding the pockets from a stiffer material than that of the bottoms of the pockets. The pockets are adapted to be pushed outwardly upon inflation of the balloon in order to deliver the therapeutic agent to a target site.

In further embodiments, the device may comprise a fluid disposed between the sheath and the balloon. The device may be adapted such that, upon inflation of the balloon and expansion of the sheath, the fluid forces the pockets to be pushed outwardly. Additionally or alternatively, the device may comprise a shape memory material disposed under each pocket, wherein the shape memory material is expandable to force the pockets to be pushed outwardly.

In further embodiments, a drug eluting balloon device comprises an inflatable balloon and a longitudinal sheath disposed around the balloon, the longitudinal sheath being constructed of a plurality of layers of material. Openings may be formed in the layers for construction of drug reservoirs. Additionally or alternatively, the layers may have substantially different resting diameters and a plurality of semi-compliant strands may be provided in order to form pockets in the sheath.

The invention may be embodied in numerous devices and through numerous methods and systems. The following detailed description, taken in conjunction with the drawings, discloses examples of the invention. Other embodiments, which incorporate some or all of the features as taught herein, are also possible.

BRIEF DESCRIPTION OF THE DRAWINGS

The present invention will become more fully understood from the following description and its accompanying drawings. These drawings are provided by way of illustration only and are not limiting of the present invention. The drawings for this application are as follows.

DETAILED DESCRIPTION

The present invention generally relates to drug delivery systems. The medicaments used in these systems may be a broad range of therapeutic agents or drugs used in the treatment of various diseases, disorders, or other medical ailments. In certain embodiments, the target site for drug delivery may be within the vasculature (such as within an artery) of a human or other mammalian body. Throughout this description and the claims that follow, the terms "therapeutic agent," "drug" and "medicament" are used interchangeably.

The following examples are merely a few of many possible embodiments and are in no way limiting of the present invention. Similarly, the headings provided below merely aid a reader in understanding the disclosure of the present invention and in no way limit the present invention.

A. First Embodiment

Figure 1:
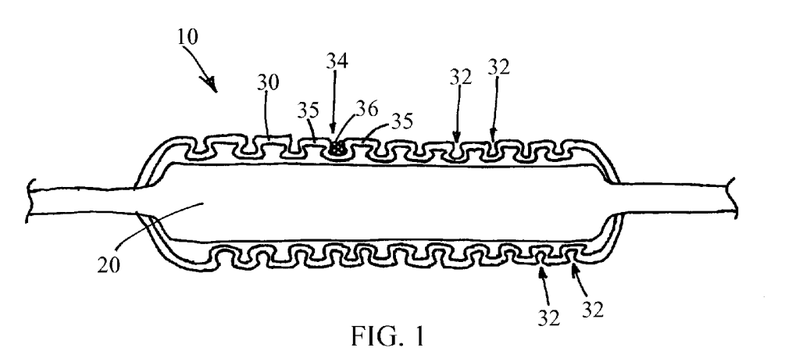
FIG. 1 shows a side sectional view of a drug eluting balloon device in a first position in accordance with certain embodiments of the present invention.
Figure 2:
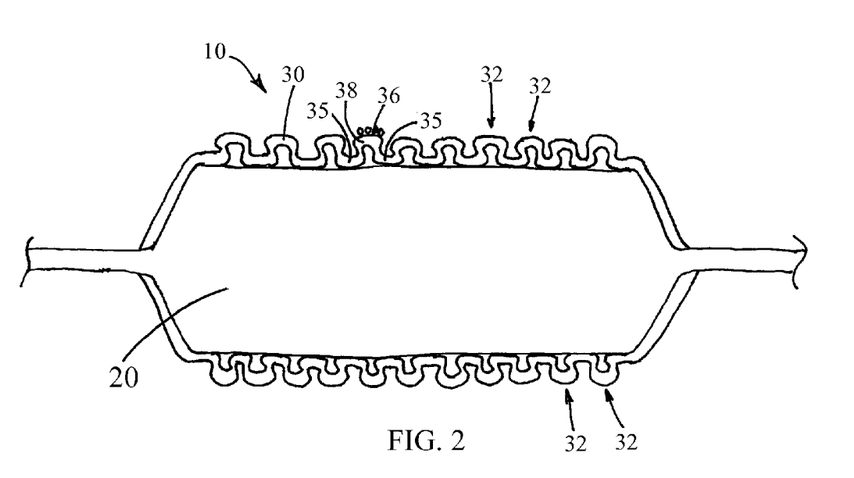
FIG. 2 shows a side sectional view of the drug eluting device of FIG. 1 in a second position.

One example of a drug eluting balloon device in accordance with certain embodiments of the present invention is a balloon catheter as shown in FIGS. 1 and 2.

FIGS. 1 and 2 show a drug eluting balloon device in the form of a balloon catheter 10 comprising an inflatable balloon 20 and a longitudinal sheath 30. The balloon 20 is inflatable from a substantially deflated position, which is shown in FIG. 1, to a substantially inflated position, which is shown in FIG. 2. The balloon 20 may be made in any suitable configuration and of any suitable material as is known in the art. In this embodiment, balloon 20 is made from a non-compliant material such as polyurethane or nylon. The balloon may be of a folded type, or it may be non-folded. Inflation of the balloon may be accomplished in manners known in the art with respect to the inflation of balloon catheters.

The longitudinal sheath 30 is disposed around the balloon 20. The longitudinal sheath 30 is expandable from a first position, which is shown in FIG. 1, to a second position, which is shown in FIG. 2. As shown in FIG. 1, when the balloon 20 is in the substantially deflated position, the sheath 30 is in the first position. As shown in FIG. 2, when the balloon 20 is inflated to the substantially inflated position, the sheath 30 is expanded to the second position.

The sheath 30 may be in the shape of a tube-like member, and it may be open-ended or closed-ended. In the embodiment shown in FIGS. 1 and 2, the sheath 30 is bonded at its proximal and distal ends to the shaft or balloon of the balloon catheter. The sheath 30 may be made of a compliant material, such as a relatively soft polyurethane, silicone, or TECOTHANE® (produced by The Lubrizol Corporation). The sheath 30 comprises a plurality of drug delivery areas 32. The drug delivery areas 32 may be spaced both radially and longitudinally along the sheath 30. These drug delivery areas 32 may have a number of configurations and may vary in shape and depth to accommodate the desired medicament.

In one configuration, the drug delivery areas 32 may have a shape generally resembling that of a teat for a baby's bottle. Thus, as can be seen in FIG. 2, each drug delivery area 32 is in the form of a protrusion that may have a generally bulbous or half-dome shape. This is the stable condition of the sheath 30. The operation of the drug delivery areas 32 can be explained by analogy to the teat for a baby's bottle. When the end of the teat is pressed inwardly, the end of the teat inverts, and it will stay in this inverted position as a quasi-stable condition. That is, it will stay inverted when released; however, when acted upon by an appropriate outside force, it will revert back to its original condition by its own force. Thus, the inversion stores elastic energy, and, when acted upon, the teat will self-invert back to its stable condition.

With respect to the drug delivery areas 32, in a stable condition of the sheath 30, the drug delivery areas 32 of the sheath 30 protrude outwardly as protrusions (as shown in FIG. 2). The protrusions are adapted to be pressed inwardly to form the pockets, as shown by the drug delivery areas 32 in FIG. 1. When the drug delivery areas 32 of the sheath 30 are in the form of pockets, as shown in FIG. 1, the pockets are in a quasi-stable condition.

When the sheath 30 is in the first position and the drug delivery areas 32 are in the form of pockets (FIG. 1), the drug delivery areas 32 are adapted to contain a therapeutic agent. FIG. 1 shows one of the pockets 34 containing a therapeutic agent 36. For simplicity, therapeutic agent is shown in only one of the pockets, but it will be appreciated that all of the pockets may be loaded with a therapeutic agent.

Upon inflation of the balloon 20 and consequent expansion of the sheath 30, the drug delivery areas 32 invert from pockets into protrusions, such that the drug delivery areas 32 are adapted to deliver the therapeutic agent 36 to a target site. Thus, by comparison of FIG. 1 to FIG. 2, it can be seen that the pocket 34 has self-inverted into a protrusion 38, to assist in the delivery of the therapeutic agent 36 to the target site. Thus, expansion of the sheath 30 from the first position (FIG. 1) to the second position (FIG. 2) causes the drug delivery areas 32 to self-invert from the pockets 34 into the protrusions 38.

In order to help facilitate the activation of the drug delivery areas 32 from pockets 34 into protrusions 38, in some embodiments the areas 35 of the sheath surrounding the pockets 34 of the sheath may be made stiffer than the pockets 34 of the sheath. Thus, the material that forms the pockets 34 will stretch more easily than the material of the surrounding areas 35. Because of this, the surrounding areas 35 are more resistant to expansion, and when an internal force is applied to the sheath, the difference in resistance to expansion will help facilitate the inversion of the drug delivery areas 32 from pockets 34 into protrusions 38.

The therapeutic agent 36 may be a broad range of drugs or other therapeutic agents to be delivered to a target site. A number of therapeutic agents are known for treatment of areas within the body, such as within the vasculature. As one example, paclitaxel may be used. In certain embodiments, in order to assist with drug delivery, the sheath 30 may be made of a hydrophobic material. This can help minimize adherence of certain therapeutic agents to the sheath.

In certain embodiments, the device may further comprise a reservoir for containing the therapeutic agent and for supplying therapeutic agent to the pockets 34. The reservoir may be adapted to refill the pockets 34 with therapeutic agent 36. For example, after a first balloon expansion and drug delivery, the balloon may be deflated, at which time therapeutic agent 36 flows from the reservoir into the pockets to refill them. Then, the balloon may be inflated a second time for a second drug delivery. This process may be repeated several times for successive drug applications.

An example process of manufacturing an embodiment as shown in FIGS. 1 and 2 is as follows. First, the sheath 30 of compliant material is molded in the general shape of a tube with a plurality of outwardly-extending protrusions 38. Then, the ends of the protrusions 38 are depressed to form a plurality of pockets 34. The sheath 30 may be placed on the balloon before or after this step. Then, therapeutic agent 36 is loaded into the pockets 34. This may be done, for example, by a drop-on-demand process as is known in the art.

An example of a process of using an embodiment as shown in FIGS. 1 and 2 is as follows. First, the deflated balloon 20 with the sheath 30 on it is delivered to a site within the vasculature in a manner as is known in the art. Because the therapeutic agent 36 is protected within pockets 34, loss of therapeutic agent during tracking through the vasculature is minimized or prevented. Then, when the balloon 20 is at the target site, the balloon 20 is inflated, thereby expanding the sheath 30. This causes the pockets 34 to self-invert into protrusions 38, as shown in FIG. 2, thereby delivering therapeutic agent to the target site, such as the inner wall of a blood vessel.

B. Second Embodiment

Figure 3:
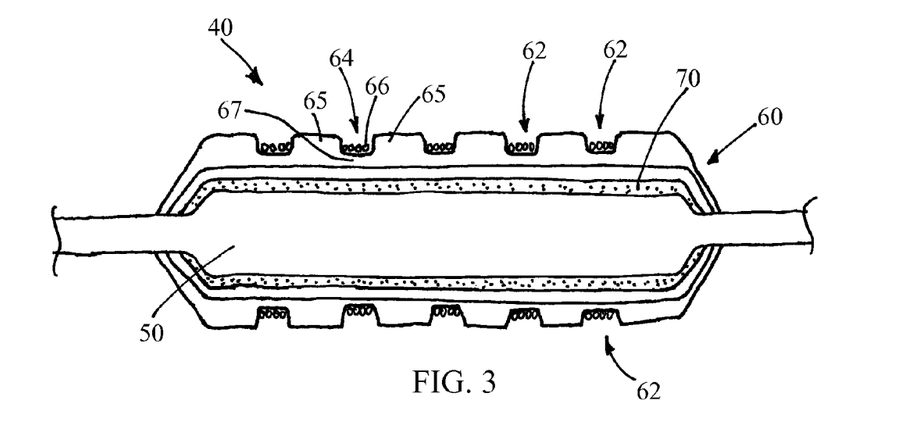
FIG. 3 shows a side sectional view of a drug eluting balloon device in a first position in accordance with certain further embodiments of the present invention.
Figure 4:
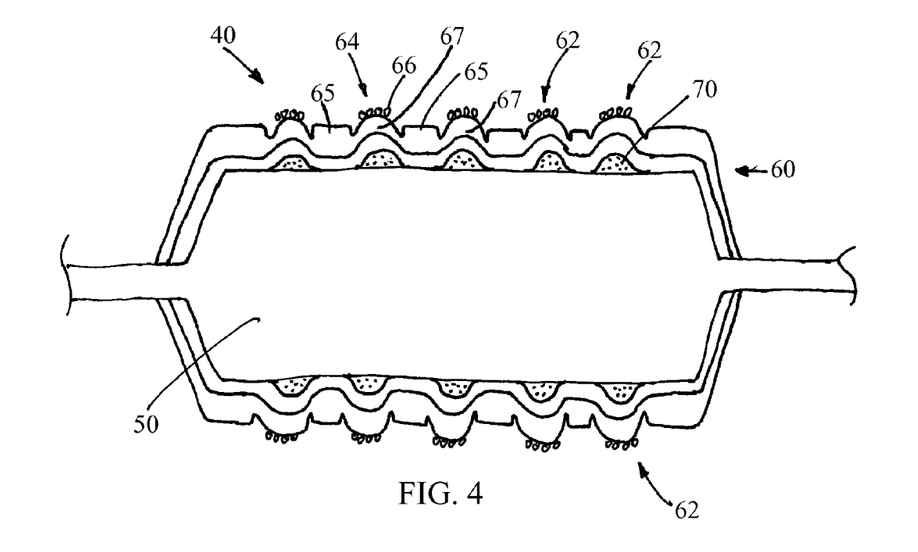
FIG. 4 shows a side sectional view of the drug eluting device of FIG. 3 in a second position.

Another example of a drug eluting balloon device in accordance with certain embodiments of the present invention is a balloon catheter as shown in FIGS. 3 and 4.

FIGS. 3 and 4 show a drug eluting balloon device in the form of a balloon catheter 40 comprising an inflatable balloon 50 and a longitudinal sheath 60. The balloon 50 is inflatable from a substantially deflated position, which is shown in FIG. 3, to a substantially inflated position, which is shown in FIG. 4. The balloon 50 may be similar to balloon 20, described above.

The longitudinal sheath 60 is disposed around the balloon 50. The longitudinal sheath 60 is expandable from a first position, which is shown in FIG. 3, to a second position, which is shown in FIG. 4. As shown in FIG. 3, when the balloon 50 is in the substantially deflated position, the sheath 60 is in the first position. As shown in FIG. 4, when the balloon 50 is inflated to the substantially inflated position, the sheath 60 is expanded to the second position.

The sheath 60 may be in the shape of a tube-like member, and it may be open-ended or closed-ended. In the embodiment shown in FIGS. 3 and 4, the sheath 60 is bonded at its proximal and distal ends to the shaft or balloon of the balloon catheter. The sheath 60 may be made of a compliant material, such as a relatively soft polyurethane, silicone, or TECO-THANE® (produced by The Lubrizol Corporation). The sheath 60 comprises a plurality of drug delivery areas 62. The drug delivery areas 62 may be spaced both radially and longitudinally along the sheath 60. These drug delivery areas 62 may have a number of configurations and may vary in shape and depth in order to accommodate the desired medicament.

In the embodiment of FIGS. 3 and 4, the drug delivery areas 62 are in the form of deformable pockets 64. The pockets 64 are adapted to contain a therapeutic agent. FIG. 3 shows the pockets 64 containing a therapeutic agent 66.

In the embodiment of FIGS. 3 and 4, the areas 65 of the sheath surrounding the pockets 64 of the sheath are stiffer than the pockets of the sheath. This stiffness can be accomplished in multiple ways. For example, as can be seen in FIGS. 3 and 4, the areas 65 of the sheath surrounding the pockets 64 of the sheath may be made thicker than the areas of the sheath forming the bottoms 67 of the pockets 64 of the sheath. Additionally or alternatively, the areas 65 of the sheath surrounding the pockets 64 of the sheath may be made from a stiffer material than that of the bottoms 67 of the pockets of the sheath. Additionally or alternatively, stiffening pieces may be embedded in the areas 65 of the sheath surrounding the pockets 64 of the sheath in order to make them stiffer than the areas of the sheath forming the bottoms 67 of the pockets 64 of the sheath.

The device 40 further comprises a fluid 70 disposed between the sheath 60 and the balloon 50. When the balloon is in the deflated state, the fluid 70 forms a fairly uniform layer between the sheath 60 and the balloon 50. However, when the balloon 50 is inflated, the pressure on the fluid 70 is increased, and the fluid 70 tends to flow to areas where it can be accommodated. Because the bottoms 67 of the pockets 64 are less stiff than other areas of the sheath 60, they can be forced outward more easily. Thus, the fluid 70 tends to press the bottoms 67 outward, in order to accommodate the fluid 70 beneath the pockets 64. Thus, the device 40 is adapted such that, upon inflation of the balloon 50 and expansion of the sheath 60, the fluid 70 forces the pockets 64 to be pushed outwardly. This can be seen in FIG. 4, in which the pockets 64 have been pushed outwardly upon inflation of the balloon 50 in order to deliver the therapeutic agent 66 to a target site.

In addition to or as an alternative to the use of the fluid 70, the device 40 may comprises a shape memory material (not shown) disposed under each pocket 64. The shape memory material is expandable so as to force the pockets 64 to be pushed outwardly. The shape memory material expands when heated to a specified temperature. This may be accomplished in several ways. For example, the shape memory material may be insulated within the sheath or other material such that it heats up after a certain known period of time after introduction of the device into the body and exposure to body temperature. Thus, the timing of its expansion and pushing on the pockets is known, and the physician or other user of the device may use the device in a manner that ensures that the balloon is in position at the target site when the expansion occurs. Alternatively, the shape memory material may be electrically connected by lead lines to an electrical source outside of the body. In this way, the shape memory material may be heated when the balloon is in position. Alternatively, the shape memory material may be manufactured to expand at a temperature slightly above body temperature, for example about 40 degrees Celsius. The fluid used to inflate the balloon may be heated to a temperature sufficient to heat the shape memory material in order to cause it to expand.

Thus, with either the use of fluid or shape memory material, or other suitable means, the pockets 64 are adapted to be pushed outwardly upon inflation of the balloon 50 in order to deliver the therapeutic agent 66 to a target site. Thus, by comparison of FIG. 3 to FIG. 4, it can be seen that the pockets 64 have been pushed outwardly, to assist in the delivery of the therapeutic agent 66 to the target site. Thus, expansion of the sheath 60 from the first position (FIG. 3) to the second position (FIG. 4) causes the drug delivery areas 62 to be pushed outwardly.

As with the therapeutic agent 36 of FIGS. 1 and 2, the therapeutic agent 66 may be selected from a broad range of drugs or other therapeutic agents to be delivered to a target site. In certain embodiments, in order to assist with drug delivery, the sheath 60 may be made of a hydrophobic material, to help minimize adherence of certain therapeutic agents to the sheath.

As with the embodiment of FIGS. 1 and 2, in certain embodiments similar to FIGS. 3 and 4, the device may further comprise a reservoir for containing the therapeutic agent and for supplying therapeutic agent to the pockets 64. The reservoir may be adapted to refill the pockets 64 with therapeutic agent 66. For example, after a first balloon expansion and drug delivery, the balloon may be deflated, at which time therapeutic agent 66 flows from the reservoir into the pockets 64 to refill them. Then, the balloon may be inflated a second time for a second drug delivery. This process may be repeated several times for successive drug applications.

An example process of manufacturing an embodiment as shown in FIGS. 3 and 4 is as follows. First, the sheath 60 of compliant material is molded in the general shape of a tube with a plurality of pockets 64. Alternatively, the sheath 60 may be made by extrusion, with the pockets 64 subsequently formed therein. The sheath 60 may be placed on the balloon before or after this step. The fluid 70 may be injected into the space between the balloon 50 and sheath 60, after which the area of injection is sealed. Next, therapeutic agent 66 is loaded into the pockets 64. This may be done, for example, by a drop-on-demand process as is known in the art.

An example of a process of using an embodiment as shown in FIGS. 3 and 4 is as follows. First, the deflated balloon 50 with the sheath 60 on it is delivered to a site within the vasculature in a manner as is known in the art. Because the therapeutic agent 66 is protected within pockets 64, loss of therapeutic agent during tracking through the vasculature is minimized or prevented. Then, when the balloon 50 is at the target site, the balloon 50 is inflated, thereby expanding the sheath 60. This causes the pockets 64 to protrude outwardly, as shown in FIG. 4, thereby delivering therapeutic agent 66 to the target site, such as the inner wall of a blood vessel.

It will be appreciated that in the embodiments of FIGS. 1-4, the device comprises means to push the therapeutic agent outwardly upon inflation of the balloon and expansion of the sheath. In FIGS. 1-2, the means to push the therapeutic agent outwardly upon inflation of the balloon and expansion of the sheath comprises the construction of the pockets themselves. In FIGS. 3-4, the means to push the therapeutic agent outwardly upon inflation of the balloon and expansion of the sheath comprises a component that pushes the bottom of the pocket outwardly. In the illustrations, that component is the fluid 70, but the component may alternatively be a shape memory material or other suitable component.

C. Third Embodiment

Figure 5A:
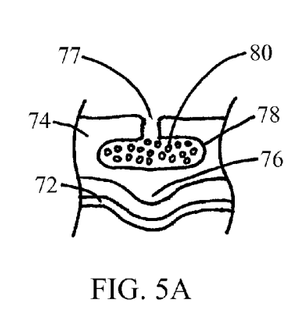
FIG. 5A shows a side sectional view of one pocket of a drug eluting balloon device in a first position in accordance with certain further embodiments of the present invention.
Figure 5B:
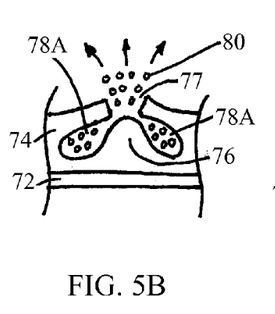
FIG. 5B shows the pocket of FIG. 5A in a second position.
Figure 5C:
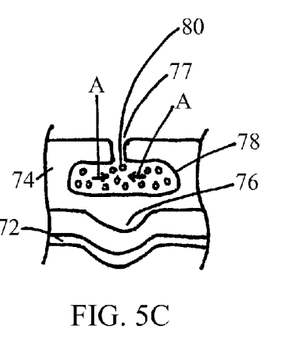
FIG. 5C shows the pocket of FIG. 5A returned to the first position after a first drug delivery.

Another example of a drug eluting balloon device in accordance with certain embodiments of the present invention is a balloon catheter having pockets as shown in FIGS. 5A-5C. Such a construction allows the balloon catheter to deliver drug on a first inflation, then be deflated, and then deliver more drug on a second inflation and potentially on subsequent inflations as well.

FIG. 5A shows a side sectional view of one pocket of a drug eluting balloon device that may be used with a balloon catheter similar to the balloon catheters described above with respect to FIGS. 1-4. As with those catheters, a drug eluting balloon device having the pocket of FIG. 5A is in the form of a balloon catheter comprising an inflatable balloon 72 and a longitudinal sheath 74. The balloon 72 is inflatable from a substantially deflated first position, which is shown in FIGS. 5A and 5C, to a substantially inflated position, which is shown in FIG. 5B. The balloon 72 may be similar to balloon 20, described above.

The longitudinal sheath 74 is disposed around the balloon 72. The longitudinal sheath 74 is expandable from a first position, which is shown in FIGS. 5A and 5C, to a second position, which is shown in FIG. 5B. As shown in FIG. 5A, when the balloon 72 is in the substantially deflated position, the sheath 74 is in the first position. As shown in FIG. 5B, when the balloon 72 is inflated to the substantially inflated position, the sheath 74 is expanded to the second position.

The sheath 74 may be in the shape of a tube-like member, and it may be open-ended or closed-ended. As in the embodiments shown in FIGS. 1-4, the sheath 74 may be bonded at its proximal and distal ends to the shaft or balloon of the balloon catheter. The sheath 74 may be made of a compliant material, such as a relatively soft polyurethane, silicone, or TECOTHANE® (produced by The Lubrizol Corporation). The sheath 74 comprises a plurality of drug delivery areas in the form of pockets 78, which may be spaced both radially and longitudinally along the sheath 74. FIGS. 5A-5C show the pocket 78 containing a therapeutic agent 80. Each pocket 78 has a relatively large drug retention area corresponding to a relatively narrow opening 77 in the sheath through which drug may be ejected. The opening 77 may be in a central location or another suitable location relative to the drug retention area.

In the embodiment of FIGS. 5A-5C, the sheath has a protrusion 76 below each pocket 78. When the balloon 72 is in the deflated state, the balloon 72 does not press on the protrusions 76. However, when the balloon 72 is inflated, as shown in FIG. 5B, the balloon presses on the protrusions 76, which causes the pockets 78 to deform. Thus, the protrusion 76 tends to press the bottoms of the pockets 78 outward. As can be seen in FIG. 5B, when this happens, only a portion of the therapeutic agent 80 is ejected from each pocket 78. That is, drug 80 that was in a central drug delivery area of the pocket 78 is pushed out through the opening 77.

At the same time, the protrusion 76 forms an obstruction which partially or completely blocks the opening 77 of the pocket 78 with respect to the remainder 78A of the pocket 78. In this manner, this remaining part of the pocket 78 remains as a reservoir 78A for drug that is retained by the pocket 78.

When the balloon 72 is deflated, as shown in FIG. 5C, the pocket 78 returns to its original position, similar to that shown in FIG. 5A. When this happens, the protrusion 76 returns to its original position, thereby removing the obstruction from the pocket 78. Thus, the drug 80 is able to redistribute itself within the pocket 78, as shown by the arrows A in FIG. 5C. From here, the balloon 72 can be expanded again, to deliver another portion of the drug 80.

Thus, in the embodiment of FIGS. 5A-5C, the pockets 78 are adapted to have reservoirs 78A that refill a delivery area of the pockets 78 with therapeutic agent 80. Thus, after a first balloon expansion and drug delivery, the balloon may be deflated, at which time therapeutic agent 80 flows from the reservoir 78A into the delivery areas of the pockets 78, thereby refilling them. Then, the balloon may be inflated a second time for a second drug delivery. This process may be repeated several times for successive drug applications.

Figure 6:
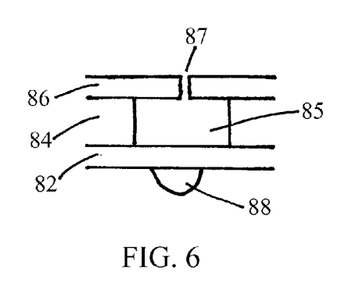
FIG. 6 shows an example of a construction of a pocket.

An example of a process of manufacturing an embodiment as shown in FIGS. 5A-5C is illustrated by the example construction of FIG. 6. The sheath 74 can be constructed out of three layers, a bottom layer 82 which remains intact, a middle layer 84 in which large openings 85 are made in order to function as the drug retention areas of the pockets, and a top layer 86, in which small openings 87 are made above the large openings 85. The openings may be any suitable shape and may be made by any suitable means, e.g., by an excimer laser. The three layers 82, 84 and 86 can be adhered together, e.g., by melting or glueing, to form the final sheath. The step of filling the pockets of the sheath with the drug can be done after first adhering the bottom and middle layers together, or the drug can be loaded into the pockets after all three layers are adhered together.

The material of the layers 82, 84, 86 may be the same or different. The thicknesses of the three layers 82, 84, 86 may be the same or different. For example, layer 82 may comprise 10% of the total thickness of the sheath, layer 84 may comprise 80% of the total thickness of the sheath, and layer 86 may comprise the remaining 10% of the total thickness of the sheath (e.g., thicknesses of 0.5 micrometer, 4 micrometers and 0.5 micrometer, respectively). Alternatively, each layer 82, 84, 86 may comprise one-third of the total thickness of the sheath (e.g., thicknesses of 2 micrometers, 2 micrometers and 2 micrometers, respectively).

A protrusion 88 may be adhered below each pocket, to function as the protrusion 76 in FIGS. 5A-5C. This protrusion may be formed in any suitable manner, for example by dropping liquid material onto the inverted sheath at the appropriate location, which liquid material then solidifies.

Figure 7:
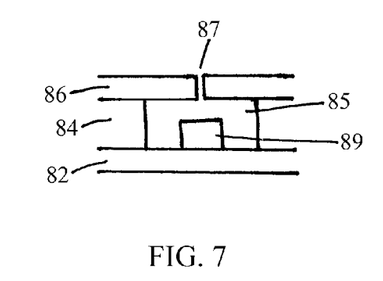
FIG. 7 shows another example of a construction of a pocket.

FIG. 7 shows another manner of constructing a sheath similar to the embodiment of FIG. 6. In FIG. 7, however, the protrusion 89 is formed within the construction of the sheath.

As in FIG. 6, the sheath is constructed from three films, a thick middle film 84 and two thin outer films 82, 86. The large openings 85 are made in the middle layer 84, and the middle layer 84 is placed on and adhered to the bottom thin layer 82. Then, hard push elements 89 are placed in the holes 85, the push elements 89 being thinner than the middle film 84 (e.g., 50% of the thickness). The push elements 89 may be adhered to the bottom layer 82. After this, the top layer 86 may be adhered on top of the middle layer 84, and holes 87 may be made above the push elements 89, e.g., by an excimer laser. In the event a laser is used, the push elements 89 can be made out of a material that is unaffected by the laser, for example out of metal or ceramic. The push elements 89 may be made out of a radiopaque material, such as gold, platinum or tungsten.

An example of a process of using an embodiment as shown in FIG. 5A-5C, 6 or 7 is as follows. First, the deflated balloon with the sheath on it is delivered to a site within the vasculature in a manner as is known in the art. Because the therapeutic agent is protected within pockets, loss of therapeutic agent during tracking through the vasculature is minimized or prevented. Then, when the balloon is at the target site, the balloon is inflated, thereby expanding the sheath. This causes the protrusions to force some of the drug out of the pockets. Then, the balloon is deflated, allowing the drug remaining in the pockets to be redistributed within the pockets. Then the balloon may undergo one or more subsequent inflations/deflations for further drug deliveries.

D. Fourth Embodiment

Figure 8A:
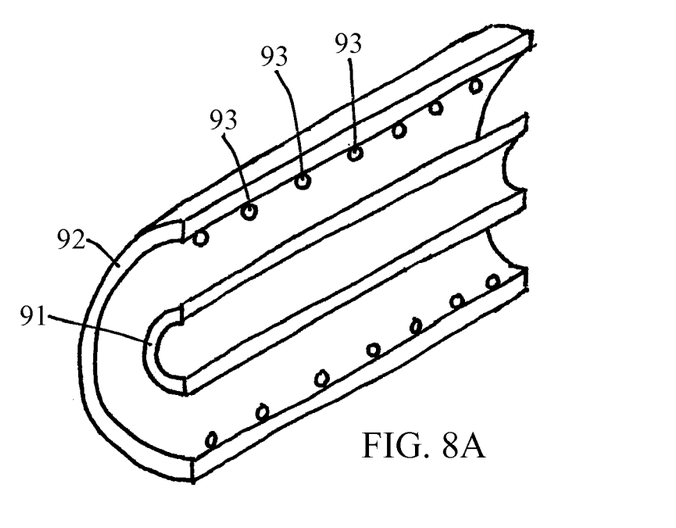
FIG. 8A shows a sectional view of elements used to construct certain further embodiments of the present invention.
Figure 8B:
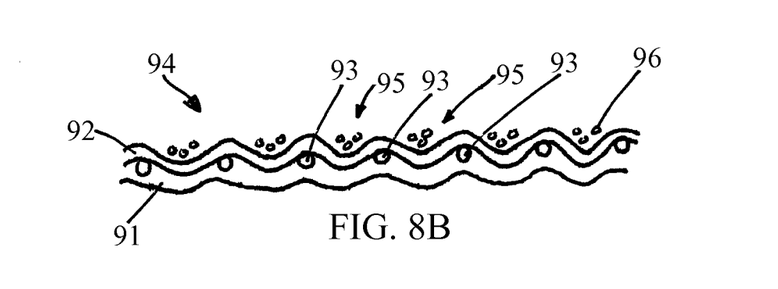
FIG. 8B shows a partial side sectional view of a device in accordance with the construction of FIG. 8A in a first position.

Another example of a drug eluting balloon device in accordance with certain embodiments of the present invention is a balloon catheter having pockets 95 as shown in FIG. 8B, with FIG. 8A showing elements used to construct the embodiment.

As shown in FIG. 8A, the construction includes two tubular compliant layers 91, 92 whereby the central layer 91 has a much smaller resting diameter than the outer layer 92. Semi-compliant circular fibers or strands 93 having a resting diameter substantially similar to that of the outer layer are also provided. To form the sheath, the central layer 91 is inflated to match the diameter of the outer layer 92, and the layers are adhered together, e.g., by melting. The strands 93 are held between the bonded layers 91, 92. When adhered, the layers form a combined sheath 94. The resting diameter of the combined sheath 94 is between the resting diameters of the inner layer 91 and outer layer 92. Thus, when assembled into the sheath 94, the outer layer 92 is under compression and the inner layer 91 is under tension. Because the strands 93 resist compression more than the outer layer 92, the resulting sheath—shown in a resting state in FIG. 8B—has depressions or pockets 95 between the strands 93. These pockets 95 can be filled with a drug 96.

Figure 8C:
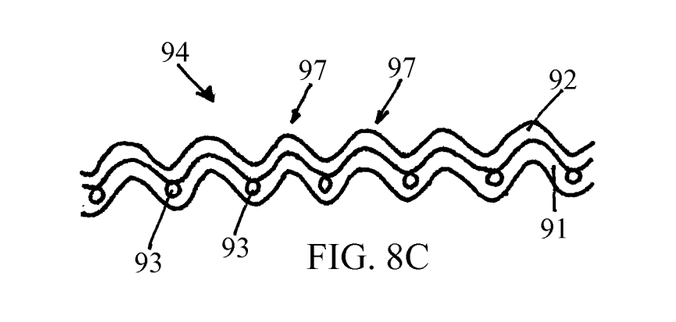
FIG. 8C shows a partial side sectional view of the device of FIG. 8B in a second position.

In use, the sheath 94 can be expanded by a balloon similar to the other embodiments described above. When the balloon expands the sheath 94 to a diameter which is larger than the initial diameter of the outer layer 92, the opposite situation is created because the strands 93 resist expansion more than the outer layer 92. Thus, the pockets 95 filled with drug 96 become protrusions 97, forcing the drug out for delivery to the target location.

Non-limiting examples of suitable compliant materials (for example, for use in the various sheaths described above) include polymeric materials such as polyamide, thermoplastic polyamide, polyesters, polyphenylene sulfides, polyethylene terephthalate, HDPE or Pebax. Other non-limiting examples include elastic materials such as silicone rubber or latex.

The devices and methods disclosed herein may be used in conjunction with a broad variety of medicaments to treat various diseases or medical conditions. Non-limiting examples of suitable medicaments include paclitaxel, everolimus, and other members of the limus family. Other non-limiting examples of therapeutic agents that may be used in conjunction with the present invention include the therapeutic agents identified in U.S. Pat. No. 7,070,613 (issued Jul. 4, 2006 to Weber, et al.) and in U.S. Patent Application Publication No. 2011/0054443 (published Mar. 3, 2011), each of which is incorporated herein by reference.

What is claimed is:

1. A drug eluting balloon device, comprising:
   an inflatable balloon, inflatable from a substantially deflated position to a substantially inflated position; and
   a longitudinal sheath disposed around the balloon, the longitudinal sheath being expandable from a first position to a second position;
   wherein when the balloon is in the substantially deflated position the sheath is in the first position, and wherein when the balloon is inflated to the substantially inflated position the sheath is expanded to the second position;
   wherein the sheath comprises a plurality of drug delivery areas;
   wherein in a stable condition of the sheath, the drug delivery areas of the sheath protrude outwardly as protrusions;
   wherein the protrusions are adapted to be pressed inwardly to an inverted position storing elastic energy;
   wherein when the sheath is in the first position, the drug delivery areas are in the inverted position in the form of pockets adapted to contain a therapeutic agent; and
   wherein the drug delivery areas are adapted such that, upon inflation of the balloon and expansion of the sheath from the first position to the second position, the stored elastic energy is released, whereby the drug delivery areas self-invert from the pockets into the protrusions, such that the drug delivery areas are adapted to deliver the therapeutic agent to a target site.

2. The device of claim 1, wherein the sheath comprises a compliant material.

3. The device of claim 1, wherein when the drug delivery areas of the sheath are in the form of pockets, the pockets are in a quasi-stable condition.

4. The device of claim 1, wherein areas of the sheath surrounding the pockets of the sheath are stiffer than the pockets of the sheath.

5. The device of claim 1, wherein the sheath is made of multiple layers.

6. The device of claim 5, wherein the sheath is made of an inner layer and an outer layer, the inner layer having a smaller resting diameter than the outer layer.

7. The device of claim 1, further comprising a reservoir adapted to refill the pockets with therapeutic agent.

8. A drug eluting balloon device, comprising:
   an inflatable balloon, inflatable from a substantially deflated position to a substantially inflated position; and
   a longitudinal sheath disposed around the balloon, the longitudinal sheath being expandable from a first position to a second position; and
   a fluid disposed between the sheath and the balloon;
   wherein when the balloon is in the substantially deflated position the sheath is in the first position, and wherein when the balloon is inflated to the substantially inflated position the sheath is expanded to the second position;
   wherein the sheath comprises a plurality of pockets containing a therapeutic agent;
   wherein areas of the sheath surrounding the pockets of the sheath are stiffer than the pockets of the sheath;
   wherein when the balloon is in the deflated state, the fluid forms a fairly uniform layer between the sheath and the balloon; and
   wherein the drug eluting balloon device is adapted such that, upon inflation of the balloon and expansion of the sheath from the first position to the second position, the fluid flows to areas beneath the pockets and pushes the pockets outwardly in order to deliver the therapeutic agent to a target site.

9. The device of claim 8, wherein the sheath comprises a compliant material.

10. The device of claim 8, wherein areas of the sheath surrounding the pockets of the sheath are thicker than the areas of the sheath forming the bottoms of the pockets of the sheath.

11. The device of claim 8, wherein areas of the sheath surrounding the pockets of the sheath are made of a stiffer material than the bottoms of the pockets of the sheath.

12. The device of claim 8, wherein the sheath comprises a hydrophobic material.

13. The device of claim 8, further comprising a reservoir adapted to refill the pockets with therapeutic agent.

\* \* \* \* \*